(12) United States Patent
Janoff et al.

(10) Patent No.: US 6,261,792 B1
(45) Date of Patent: Jul. 17, 2001

(54) LIPID-DEPENDENT DIAGNOSTIC ASSAYS

(75) Inventors: Andrew S. Janoff, Yardley, PA (US); Joyce Rauch, Montreal (CA); Theodore F. Taraschi, Tabernacle, NJ (US)

(73) Assignee: The Liposome Company, Inc., Princeton, NJ (US)

( * ) Notice: Subject to any disclaimer, the term of this patent is extended or adjusted under 35 U.S.C. 154(b) by 0 days.

(21) Appl. No.: 08/441,567

(22) Filed: May 15, 1995

Related U.S. Application Data

(63) Continuation of application No. 08/201,718, filed on Feb. 25, 1994, now abandoned, which is a continuation of application No. 07/723,497, filed on Jun. 28, 1991, now abandoned, which is a continuation-in-part of application No. 07/623,340, filed on Dec. 7, 1990, now abandoned.

(51) Int. Cl.$^7$ ..................................................... C12Q 1/56
(52) U.S. Cl. ............................................. 435/13; 435/962
(58) Field of Search ........................ 435/13, 962; 436/69, 436/175, 506, 811, 825

(56) References Cited

U.S. PATENT DOCUMENTS

| | | | |
|---|---|---|---|
| 3,983,004 | 9/1976 | Trobisch et al. | 435/13 |
| 4,006,057 | 2/1977 | Sano et al. | 435/113 |
| 4,458,015 | 7/1984 | Jenig et al. | 435/184 |
| 4,543,339 | 9/1985 | O'Neill | 435/13 |
| 4,666,831 | 5/1987 | Janoff et al. | 435/13 |
| 4,698,299 | * 10/1987 | Janoff | 435/13 |
| 4,839,111 | * 6/1989 | Huang | 264/4.6 |
| 4,877,741 | 10/1989 | Babcock et al. | 435/13 |

FOREIGN PATENT DOCUMENTS

| | | | |
|---|---|---|---|
| 0 303 515 | 2/1989 | (EP) | G01N/33/544 |

OTHER PUBLICATIONS

Madden T. D., Stabilization of Bilayer Structure . . . Biochem Biophys ACTA 684 (1982) 149–153.*

T. D. Madden et al., "Stabilization of Bilayer Structure . . ." *Biochimica et Biophysica Acta*, 684 (1982) pp. 149–153.*

Rauch, et al., Human Hydridoma Lupus Anticogalent Distinguish between Lamellar and Hexagonal Phase Lipid Systems J. of Biol. Chem. vol. 261, No. 21, pp. 9672–9677, 1986.

Stryer, *Biochemistry*, 3rd Ed., 1988, pp. 300 and 301.

Madden, et al. "Stabilization of Bilayer Structure for Unsaturated Phosphatidylethanolamines by Detergents", Biochimica et Biophysica Acta, 684 (1982) 149–153.

T. Exner, et al., "Studies on Phsopholipids in the Action of a Lupus Coagulation Inhibitor", Pathology, vol., 7, pp. 319–328 (1975).

P. Thiagarajan, et al., "Monoclonal Immunoglobulin M–lambda Coagulation Inhibitor with Phospholipid Specificity", J. Clin. Invest., vol. 66, Sep. 1980, pp. 397–405.

P. F. Sparling, "Diagnosis and Treatment of Syphilis," New England Journal of Medicine, vol. 284, pp. 642–653 (1971).

J. Folch, "Brain Cephalin, A Mixture of Phosphatides. Separation from it of Phosphatidyl Serine, Phosphatidyl Ethanolamines, and a Fraction Containing an Inositol Phosphatide," J. Biol. Chem., vol. 146, pp. 35–41 (1942).

Rauch, et al., "Distinguishing Plasma Lupus Anticoagulants from Anti–Factor Antibodies Using Hexagonal (II) Phase Phospholipids," Thrombosis and Haemostasis, 62(3), pp. 892–896 (1989).

Kahn, "Orientation of Liquid Crystals by Surface Coupling Agents," Appl. Phys. Lett., 22:8, 386–8 (1973).

* cited by examiner

*Primary Examiner*—Ralph Gitomer
(74) *Attorney, Agent, or Firm*—Rosanne Goodman

(57) ABSTRACT

For use in a lipid-dependent diagnostic assay, a stable aqueous suspension of a phospholipid which normally has a hexagonal ($H_{II}$) organization when dispersed in an aqueous medium without detergent, the suspension containing the phospholipid, a detergent, and an aqueous phase. In the stable suspension, the phospholipid remains in suspension at a temperature of 25° C. for at least one hour. The suspension is suitable for providing the phospholipid to an assay for lupus anticoagulants which includes the step of pre-incubating a test sample with the phospholipid.

28 Claims, 2 Drawing Sheets

LIPID-DEPENDENT DIAGNOSTIC ASSAYS

RELATED APPLICATIONS

This application is continuation of application Ser. No. 08/201,718 filed on Feb. 25, 1994, now abandoned which is a continuation of Ser. No. 07/723,497 filed Jun. 28, 1991, now abandoned which is a continuation-in-part of U.S. Ser. No. 07/623,340, filed Dec. 7, 1990 now abandoned.

BACKGROUND OF THE INVENTION

1. Field of the Invention

This invention relates to diagnostic assays, and in particular to diagnostic assays for lupus anticoagulants which employ phospholipids as assay reagents.

2. Description of the Related Art

A variety of diagnostic assays are known which include one or more phospholipids as assay reagents. For example, various blood coagulation tests, such as complete and partial thromboplastin times, prothrombin times, and the like, employ brain and other tissue extracts which include lipids. Similarly, the VDRL (Venereal Disease Research Laboratory) test for syphilis is based on the use of an antigen solution which includes cardiolipin, cholesterol and lecithin.

As with many assay systems, the foregoing assays suffer from the problem of false positives, i.e., for certain patients, the coagulation tests give results indicative of a coagulation problem, when, in fact, the patient's clotting mechanisms are normal, or, in the case of the VDRL test, a patient appears to have syphilis, but is, in fact, syphilis free.

Prior studies have established a correlation between these false positives and certain diseases. For example, blood samples from patients having the autoimmune disease systemic lupus erythematosus (SLE) often have prolonged coagulation times, even though clinically the patients do not exhibit bleeding tendencies and, indeed, in some cases may suffer from thrombotic episodes. The blood of such patients is said to contain "lupus anticoagulants", "coagulation inhibitors", "lupus inhibitors", or "circulating inhibitors". See T. Exner et al., "Studies on Phospholipids in the Action of a Lupus Coagulation Inhibitor," *Pathology*. Vol. 7, pages 319–328 (1975); and P. Thiagarajan et al., "Monoclonal Immunoglobulin M-lambda Coagulation Inhibitor with Phospholipid Specificity," *J. Clin. Invest.*, Vol. 66, September 1980, pages 397–405.

It is presently believed that these "inhibitors" are in fact antibodies against phospholipids which are produced by the immune system of patients suffering from SLE. See P. Thiagarajan et al., supra. Similar anti-phospholipid antibodies have been found in the sera of patients suffering from other autoimmune diseases, such as connective tissues disease, Hashimoto's thyroiditis, rheumatoid arthritis, and the like. See P. F. Sparling, "Diagnosis and Treatment of Syphilis," *New England Journal of Medicine*, Vol. 284, pages 642–653 (1971). Accordingly, patients with these diseases are also likely to give false positives when subjected to lipid-dependent diagnostic assays.

Efforts have been made in the past to solve the problem of false positives in lipid-dependent assays, and, in particular, lipid-dependent coagulation assays, but with only limited success. Thus, Exner et al., supra, reported that the effect of lupus inhibitor on the Russell viper venom coagulation test could be partially corrected by adding to the reagent mixture what Exner referred to as "partially characterized" phospholipids obtained from bovine cephalin using the Folch procedure. See J. Folch, "Brain Cephalin, A Mixture of Phosphatides. Separation from it of Phosphatidyl Serine, Phosphatidyl Ethanolamines, and a Fraction Containing an Inositol Phosphatide," *J. Biol. Chem.*, Vol. 146, pages 35–41 (1942).

Exner tested three phospholipid fractions identified as phosphatidyl ethanolamine, phosphatidyl serine, and inositol phosphatide. As reported by Exner, at low concentrations each fraction reduced somewhat the clotting times of plasma samples containing lupus inhibitor, but not to the levels observed for normal samples. At higher concentrations, the addition of these phospholipid fractions unfortunately changed both the clotting times of the inhibitor-containing samples and the clotting times of the normal samples. That is, rather than solving the false positive problem, the addition of these phospholipids to the reagent mixture resulted in a change in the overall response, including the baseline, of the assay. Of the three phospholipid fractions tested, Exner stated that the phosphatidyl ethanolamine fraction appeared to give the best corrective effect.

In addition to the Exner work, Thiagarajan et al, supra, studied the effects on coagulation assays of purified IgM-lambda paraprotein obtained from a patient whose response to lipid-dependent coagulation tests indicated the presence in the patient's blood of a lupus-type anticoagulant. The purified paraprotein, when added to normal plasma, was found to reproduce the abnormal coagulation times observed with the patients plasma. Studies using the paraprotein indicated that it reacted with phosphatidylserine and phosphatidic acid, but that it did not react with phosphatidylcholine or phosphatidylethanolamine.

A comparison of the results reported by Thiagarajan with those reported by Exner highlights the confusing state of the art at that time. Whereas Thiagarajan et al. found that their lupus anticoagulant would not react with phosphatidylethanolamine, Exner et al. found just the opposite. Moreover, in Exner's hands, phosphatidylethanolamine distorted the basic character of the assay, as evidenced by the fact that the presence of 0.05% phosphatidylethanolamine in the reagent mixture resulted in an over 40% increase in the clotting time of normal plasma, and only a 30% decrease in the clotting time of a mixture of 90% normal plasma and 10% patient plasma (see FIG. 2A of Exner et al.).

Janoff et al., U.S. Pat. No. 4,666,831, issued May 19, 1987, incorporated herein by reference, disclosed an improved lipid-dependent diagnostic assay in which the test sample to be assayed is pre-incubated with one or more phospholipids which have a hexagonal ($H_{II}$) organization when dispersed in an aqueous phase. Alternatively, Janoff et al. pre-incubate with lipidic particles. As demonstrated by the test results presented in the Janoff patent, lipid-dependent diagnostic assays which include pre-incubation with such hexagonal ($H_{II}$) phospholipids were shown to be less likely to exhibit false positives. Among the preferred phospholipids used in the Janoff patent were dioleoylphosphatidylethanolamine (DOPE) and egg phosphatidylethanolamine (EPE). A related patent, Janoff et al., U.S. Pat. No. 4,689,299, issued Oct. 6, 1987, discloses the use of bilayer-forming lysophospholipids as an alternative pre-incubation agent in such assays.

The use of such hexagonal ($H_{II}$) phospholipids in assays is further discussed in Rauch et al., "Distinguishing Plasma Lupus Anticoagulants from Anti-Factor Antibodies Using Hexagonal (II) Phase Phospholipids," *Thrombosis and Haemostasis*, 62(3) 892–896 (1989). In this article, also incorporated by reference into the present application, Rauch demonstrates in a series of tests that egg phosphatidylethanolamine (EPE), inhibits the anticoagulating effects of Lupus anticoagulant without affecting the anticoagulating effects of other tested anticoagulants, such as anti-factor antibodies or heparin. Thus, hexagonal ($H_{II}$) phospholipids can be used in assays to specifically distinguish between Lupus anticoagulant and other anticoagulants.

In the assay process, as discussed in the Janoff et al. U.S. Pat No. 4,666,831 patent and the Rauch et al. article, a preliminary step is the preparation of a stock solution of the $H_{II}$ phospholipid suspended in a suitable aqueous carrier such as Hepes buffer. However, the hexagonal ($H_{II}$) organization of such phospholipids which makes them suitable for use in such assays also makes them very difficult to suspend in aqueous media. This is particularly true of a pure synthetic phospholipid such as DOPE, because natural phospholipids, such as EPE, often have small amounts of impurities that may improve their suspendability. Thus when $H_{II}$ phospholipids are suspended in aqueous buffer, they have been found to precipitate quickly, thus causing problems in handling. Such mixtures need to be mixed continuously to maintain the suspensions. Furthermore, the hydrated phospholipids tend to stick to the sides of glass vessels, and are thus extremely difficult to pipette.

SUMMARY OF THE INVENTION

In accordance with the present invention, there is provided a stable aqueous suspension of a phospholipid for use in an assay for lupus anticoagulants which is performed on a test sample, in which the assay includes the step of pre-incubating the test sample with the phospholipid, and in which the phospholipid has a hexagonal ($H_{II}$) organization when dispersed in an aqueous medium without detergent under the conditions of the assay, the suspension comprising (a) the phospholipid;

(b) a lupus-assay compatible detergent; and (c) an aqueous phase, wherein said phospholipid remains in suspension at a temperature of 25° C. for at least one hour.

A "lupus-assay compatible detergent" is one which in combination with a selected phospholipid meets the following criteria:

1. Inhibits lupus anticoagulant specifically; and
2. Does not interfere with the anticoagulation effects of heparin, anti-Factor antibodies, and factor deficiencies.

Good results are obtained when the detergent comprises a salt of desoxycholic acid, particularly sodium desoxycholate.

In another embodiment of the present invention, there is provided an improved lipid-dependent diagnostic assay for lupus anticoagulants which is performed on a test sample, and in which the assay comprises pre-incubating the test sample with one or more phospholipids which have a hexagonal ($H_{II}$) organization when dispersed in an aqueous phase without detergent under the conditions of the assay, the improvement comprising:

providing said phospholipids in combination with a lupus-assay compatible detergent, the combination of phospholipid and detergent forming a stable aqueous suspension when mixed with said aqueous phase under the conditions of the assay, in which suspension said phospholipids can remain in suspension at a temperature of 25° C. for at least one hour; and pre-incubating the test sample with said combination of phospholipid and lupus-assay compatible detergent.

In particular embodiments, the phospholipids are dioleoylphosphatidylethanolamine, egg phosphatidyletha-nolamine or bovine phosphatidylethanolamine. In other particular embodiments, the detergent comprises a salt of desoxycholic acid, with good results obtained using sodium desoxycholate.

In a further aspect of the present invention, there is provided an improved assay for use in determining whether a patient has lupus anticoagulants wherein the assay comprises the steps of:

(a) obtaining first and second samples of the patient's plasma;

(b) incubating the first sample with one or more phospholipids which have a hexagonal ($H_{II}$) organization when dispersed in an aqueous medium without detergent under the conditions of the assay;

(c) performing a lipid-dependent diagnostic assay on both the first and second samples, the assay producing a positive reading when used to assay a sample which contains lupus anticoagulants; and (d) comparing the results of the assays performed on the first and second samples, the presence of a normal result for the first sample and a positive result for the second sample being indicative of the patient having lupus anticoagulants; the improvement comprising:

providing the phospholipids in combination with a lupus-assay compatible detergent which can form a stable aqueous suspension comprising an aqueous phase, the phospholipids and a detergent, in which suspension said phospholipids can remain in suspension at a temperature of 25° C. for at least one hour.

Applicants have found that phospholipids which normally have a hexagonal ($H_{II}$) organization when dispersed in an aqueous medium without detergent can be made into stable aqueous suspensions by combining them with a detergent, such as a desoxycholate, and that this can be done without affecting the ability of such phospholipids to be used in lipid-dependent diagnostic assays for lupus anticoagulants, as discussed above. This result is particularly surprising, because the detergents appear to alter, at least partially, the normal hexagonal ($H_{II}$) organization of the phospholipids without significantly affecting the actions of such phospholipids in lipid-dependent assays. The ability to formulate such phospholipids into stable aqueous suspensions for use in assay procedures greatly facilitates the use of these phospholipids.

A characteristic of hexagonal ($H_{II}$) organization lipids that is believed to result in recognition by lupus anticoagulants is the relatively small radius of curvature of the surface of the lipid structures which modulates the presentation of specific epitopes of the phospholipids. In accordance with another aspect of the present invention, similar epitope modulation is achieved using a composition comprising a phosphatidylethanolamine coated onto substrate beads to produce spheres with a radius approximating the radius of curvature of hexagonal ($H_{II}$) tubes. Good results are achieved with coated spheres having a diameter of about 50 nm or less, particularly with coated spheres having a diameter of 20 nm or less, and more particularly with coated spheres having a diameter of between about 5 nm and about 20 nm. In a particular embodiment of the present invention, coated spheres with a diameter of about 13 nm are used.

DETAILED DESCRIPTION

Figure 1:
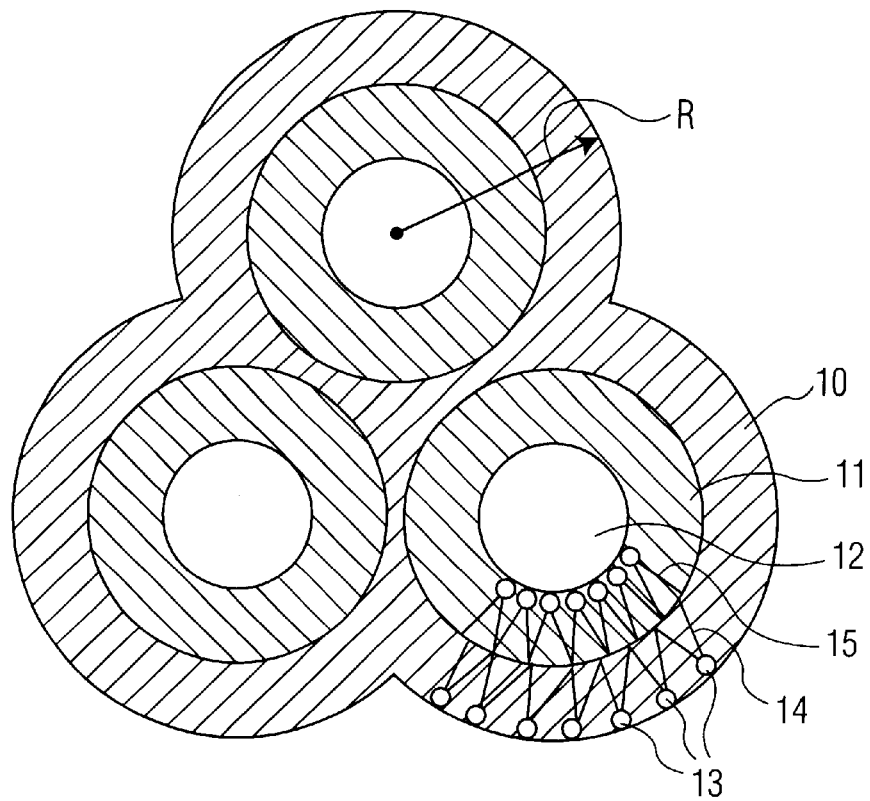
FIG. 1 is a schematic representation of a cross-section of lipid molecules in the hexagonal ($H_{II}$) orientation.

As described above, in accordance with a particular embodiment of the present invention, there is provided a stable aqueous suspension of a phospholipid for use in an assay for lupus anticoagulants which is performed on a test sample, in which the assay includes the step of pre-incubating the test sample with the phospholipid, and in which the phospholipid has a hexagonal ($H_{II}$) organization when dispersed in the test sample without detergent under the conditions of the assay, the suspension comprising (a) the phospholipid;

(b) a lupus-assay compatible detergent; and (c) an aqueous phase, wherein said phospholipid remains in suspension at a temperature of 25° C. for at least one hour.

The phospholipid is one which has a hexagonal ($H_{II}$) organization when dispersed in an aqueous medium without detergent under the conditions of the assay. Such "conditions of the assay" include, but are not limited to, temperature, concentration of all components, ionic concentrations, pH, etc. Many such assays are conducted at 37° C., and therefore for such assays the phospholipid must be in $H_{II}$ form at that temperature. Examples of phospholipids which are suitable for use in the present invention include dioleoylphosphatidylethanolamine (DOPE), egg phosphatidylethanolamine (EPE), and bovine phosphatidylethanolamine and certain phosphatidic acids. In addition, cardiolipin can be in hexagonal ($H_{II}$) phase when provided in combination with calcium ions, as is well known in the art. Of these, DOPE is particularly suitable because it is a synthetic phospholipid and thus generally freer of contaminants than the phospholipids derived from natural sources. As discussed above, it is the purity of DOPE that has also made it particularly hard to maintain in suspension and handle in assay procedures.

For purposes of this application, the stable aqueous suspensions are defined as "stable" when they stay in suspension at room temperature (25° C.) for a period of at least one hour. In fact, the suspensions used in the examples below were found to be stable for periods of four hours and even longer. Conversely, the mixtures of hexagonal ($H_{II}$) phospholipids in buffer solution without detergent were found to settle out of suspension almost immediately after cessation of agitation. Therefore, the one-hour limit clearly differentiates the suspensions of the present invention from $H_{II}$ phospholipid mixtures without detergent.

The detergents suitable for use in the present invention must be lupus-assay compatible, as previously defined, and must be able to form a stable aqueous suspension with a phospholipid. The suitability of a particular detergent for use with a selected phospholipid in the performance of a particular assay should be readily determinable by one skilled in the art. A preferred detergent for use in the present invention is a salt of desoxycholic acid, particularly sodium desoxycholate, which is used in the examples below. Good results were obtained using about 40 to 50 mol % detergent, based on the total amount of combined phospholipid and detergent.

The $H_{II}$ phospholipid suspension is used to pre-incubate a test sample for a lipid-dependent diagnostic assay for lupus anticoagulants. This process is described in detail in the Janoff et al. U.S. Pat. No. 4,666,831 patent, cited above and incorporated herein by reference. A particular assay to which the present invention is applicable are coagulation tests on human plasma as part of an activated partial thromboplastin time (APTT) assay. The present invention may also be applicable to other lipid dependent diagnostic assays such as prothrombin times, Russell viper venom times, Taipan snake venom times, and cardiolipin-dependent tests for syphilis, e.g., the VDRL test.

The stable aqueous phospholipid suspension of the present invention is of particular use in assays for determining whether a patient has lupus anticoagulants. Such assays comprise the steps of:

(a) obtaining first and second samples of the patient's plasma;

(b) incubating the first sample with a stable aqueous phospholipid suspension made in accordance with the present invention;

(c) performing a lipid-dependent diagnostic assay on both the first and second samples, the assay producing a positive reading when used to assay a sample which contains anti-phospholipid antibodies; and (d) comparing the results of the assays performed on the first and second samples, the presence of a normal result for the first sample and a positive result for the second sample being indicative of the patient having lupus anticoagulants.

The Use of Coated Beads to Mimic Hexagonal ($H_{II}$) Phosdholidids:

As discussed above, with particular reference to previously incorporated U.S. Pat. No. 4,666,831, lupus anticoagulants recognize the hexagonal ($H_{II}$) phase of phospholipids. It is believed that this phase recognition results from the orientation of the polar head groups of the lipid molecules in the hexagonal ($H_{II}$) orientation, and that this orientation modulates the presentation of specific epitopes of the phospholipids, as shown schematically in FIG. 1.

FIG. 1 is a schematic cross-section of a phospholipid, such as EPE, for example, in an array of the generally tubular structures characteristic of the hexagonal ($H_{II}$) configuration. In this configuration, an outer layer 10 of the phospholipid surrounds an inner layer 11 of the same phospholipid in a tail-group to tail-group bilayer formation. In this orientation, the polar head groups 13 of the phospholipid molecules are arrayed on the outer surface of tubular units with a radius R. This radius R shall be referred to herein as the effective radius of curvature of the phospholipid in the hexagonal ($H_{II}$) configuration. The tail groups 14 of the outer layer 10 of phospholipid molecules are held in place in tail-to-tail orientation to the tail groups 15 of the inner layer 11 of phospholipid, forming the hexagonal ($H_{II}$) bilayer configuration. It is believed that this structure, and particularly the radius of curvature R, modulates the presentation of specific epitopes of the phospholipids, and thereby results in the the specific recognition of lupus anticoagulants of the hexagonal ($H_{II}$) phase form of phospholipids.

When the phospholipid is EPE, the radius R has been determined to be about 6.5 nm. In this case, the hollow core 12 of each tube is believed to have a radius of about 2.5 nm, with the inner and outer layers of EPE each being about 2.0 nm thick. This yields a total radius R of about 6.5 nm.

The characteristic of hexagonal ($H_{II}$) organization lipids that is believed to result in recognition by lupus anticoagulants is the relatively small radius of curvature. This is believed to cause the presentation of specific epitopes of the phospholipids. That is, the head groups of the phospholipids on the surface of the hexagonal tube arrays in some manner mimic molecular entities recognized by the lupus anticoagulant, and cause the lupus anticoagulant to bind thereto.

Figure 2:
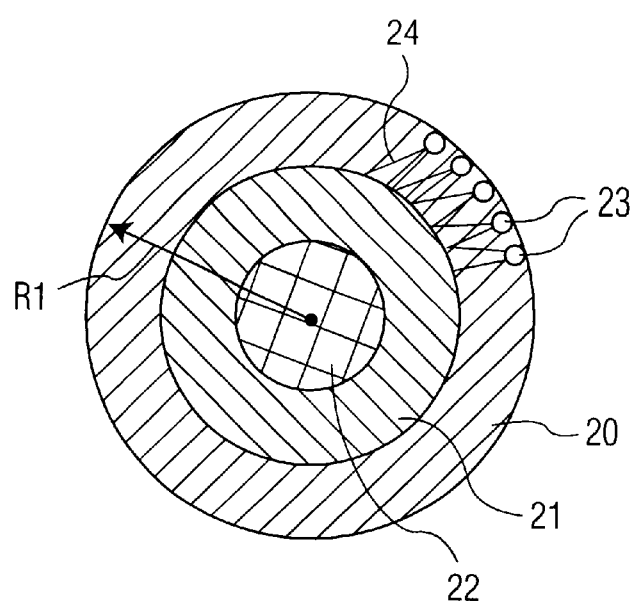
FIG. 2 is a schematic representation of a cross-secton of a lipid coated bead made in accordance with the present invention.

In accordance with the present invention, and as shown schematically in FIG. 2, similar epitope modulation is achieved with a composition prepared by coating a phosphatidylethanolamine (PE) onto substrate beads to produce spheres with a radius of curvature R' comparable to the radius of curvature R of the hexagonal ($H_{II}$) tubes shown in FIG. 1. The coated bead depicted in FIG. 2 comprises a substrate bead 22 core onto which is deposited a suitable bonding layer 21, and over which is applied a monolayer 20 of the phosphatidylethanolamine. The bonding layer 21 is made from a material which presents a non-polar outer surface to which the non-polar tail groups 24 of the phosphatidylethanolamine can bind. Thus, the outer phosphatidylethanolamine layer 20 is formed with the polar head groups 23 oriented outwardly. By preparing the spherical composition to yield the same radius of curvature as that of the hexagonal ($H_{II}$) tubes, the coated beads can effectively mimic the tubular structure of the hexagonal ($H_{II}$) organization, and thereby modulate the presentation of specific epitopes of the phosphatidylethanolamine in the same manner as the tubular structures.

Good results are achieved with coated spheres having a diameter of about 50 nm or less, particularly with coated spheres having a diameter of 20 nm or less, and more particularly with coated spheres having a diameter of between about 5 nm and about 20 nm. At diameters greater than about 50 nm, the radius of curvature of the spheres may be too large to obtain the desired recognition by lupus anticoagulants. In a particular embodiment of the present invention, coated spheres with a diameter of about 13 nm are used, to mimic the hexagonal ($H_{II}$) structure of EPE.

A key characteristic of the substrate bead 22 is that it have a small enough diameter to obtain a final coated bead with a radius R' comparable to the radius R. Good results are obtained using gold beads as the substrate, such beads being commercially available in diameters as small as 5.0 nm, and even as small as 1.0 nm in diameter. The 5.0 nm diameter gold beads approximate the diameter of the hollow core 15 of the hexagonal ($H_{II}$) orientation of EPE. Gold is also desirable because of its relative inertness. Suitable substrate beads could also be formed from polymeric materials, such as latex.

Theoretically, it would be desirable to coat a phospholipid directly onto the substrate bead. However, it was found that when a gold substrate bead is used, a bonding layer is needed to adhere the phospholipid to the substrate bead, and to obtain the desired phospholipid head-group orientation. Good results are obtained by using an organic silane to form a bonding layer onto which the phospholipid layer is deposited. Such silanization procedures are well known to those skilled in the art and are commercially available. For a discussion of the use of silanes as bonding agents, see Kahn, "Orientation of Liquid Crystals by Surface Coupling Agents," *Appl. Phys. Lett*., 22:8, 386–8 (1973). Kahn discusses the use of a silane identified as N,N-dimethyl-N-octadecyl-3-aminopropyltrimethoxysilyl chloride, also referred to as "DMOAP". DMOAP is the silane which was used in the examples of the present invention below, and was obtained from HUls America/Petrarch Systems, Bristol, Pa, under the chemical name n-octadecyldimethyl[3-(trimethoxysilyl)-propyl] ammonium chloride (50% in methanol, Catalog No. 09745).

FIG. 3 presents a schematic of a process for coating gold beads in accordance with the present invention. In FIG. 3A, a gold bead 30 is activated by immersion in dilute NaOH, to form -OH active sites 31. This activation provides adhesion sites on the gold surface to which the silane molecules can adhere. In FIG. 3B a silane solution is applied to the activated beads to form bonding layer 32. The silane molecules include non-polar organic moieties which extend outwardly from the surface of the gold. Finally, as shown in FIG. 3C, the desired phospholipid is applied to the bonding layer 32, to form a lipid monolayer 33.

The organic silane should include non-polar organic moieties compatible with the non-polar tail groups of the phosphatidylethanolamine to be deposited onto the bonding layer. In this manner, the phosphatidylethanolamine layer 33 can bind to the silane layer 32 in the same manner as the outer lipid layer 10 binds to the inner lipid layer 11 of the hexagonal ($H_{II}$) orientation phospholipid shown in FIG. 1. Good results were obtained using DMOAP as the bonding silane when palmitoyloleoylphosphatidylethanolamine ("POPE") was used as the outer coating.

The preferred phospholipids for use as the outer coating in this embodiment of present invention are the phosphatidylethanolamines. Among the suitable phosphatidylethanolamines are EPE, DOPE, and bovine phosphatidylethanolamine, all of which can naturally form into hexagonal ($H_{II}$) organization, as discussed previously herein. In addition, bilayer-forming phosphatidylethanolamines which normally form into liposomes rather than hexagonal ($H_{II}$) structures can also be used. As an example, palmitoyloleoylphosphatidylethanolamine ("POPE"), which normally forms liposomes and not hexagonal ($H_{II}$) structures, can be used.

MATERIALS AND METHODS

In a particular embodiment of the present invention, the assay for lupus anticoagulants is a human plasma coagulation test which measures activated partial thromboplastin time (APTT). In the examples which follow, a stabilized aqueous suspension of DOPE in combination with sodium desoxycholate is used to pre-incubate samples for APTT assay. The materials and methods common to the various examples were as follows.

PreDaration of Test Materials

Dioleoylphosphatidylethanolamine (DOPE) was purchased from Avanti Polar Lipids (Birmingham, Ala.). A stock solution was prepared of 50 mg/ml DOPE in $CHCl_3$ (chloroform).

Sodium desoxycholate was obtained from Fisher Scientific Co. (Montreal, Quebec). The desoxycholate was made into a stock solution of 50 mg/ml in 1:1 $CHCl_3$:MeOH (chloroform:methanol).

A stock suspension of DOPE (4 mg/ml)-sodium desoxycholate (50 mol %) was made as follows: 40 ul of the DOPE stock solution and 22 ul of the desoxycholate stock solution were placed in a round bottom glass tube and an additional 40 ul of 1:1 $CHCl_3$:MeOH was added. The solvents were then removed by evaporation under dry nitrogen for 30 minutes. The dried residue was then resuspended in 0.5 ml of 20 mM Hepes buffer (15 mM NaCl, pH 7.5), and hydrated for 15 minutes at a temperature of 37° C., and then for 45 minutes at 25° C. These temperatures are well above the lamellar to hexagonal ($H_{II}$) transition temperature of DOPE, which is less than about 10° C. The Hepes buffer was obtained from Sigma Chemical Co., St. Louis, Mo..

A stock solution of sodium desoxycholate in Hepes buffer was also prepared for use in the comparative tests. The desoxycholate/Hepes stock solution was prepared by mixing 22 ul of the desoxycholate stock solution with an additional 22 ul 1:1 $CHCl_3$:MeOH, and then removing the solvents by evaporation under dry nitrogen. Then 0.5 ml of 20 mM Hepes buffer (15 mM NaCl, pH 7.5) was added, and the composition mixed to form the desoxycholate/Hepes stock solution.

Activated partial thromboplastin time (APTT) reagent, a platelet factor 3 reagent (partial thromboplastin) plus particulate activator, was obtained from Organon Teknika, Inc., Scarborough, Ontario (hereinafter referred to as "Organon"). The reagent was diluted 1/32 in 20 mM Hepes buffer (15 mM NaCl, pH 7.5).

Human Plasmas

Blood was drawn into blue stopper blood collection tubes (4.5 ml total volume/tube) (Vacutainer Systems, Rutherford, N.J.) containing 0.5 ml 3.8% buffered sodium citrate. The blood was then centrifuged for 30 minutes at 1800 rpm (800×g) at room temperature on an IEC tabletop centrifuge to obtain platelet-poor plasma. Verify normal citrated plasma (pooled normal human plasma) was obtained from Organon. Lupus anticoagulant-containing plasmas were obtained from 10 patients with systemic lupus erythematosus (SLE) from the McGill Lupus Registry. All patients fulfilled the 1982 revised American Rheumatism Association criteria for the classification of SLE. A circulating lupus anticoagulant was considered to be present if the APTT was ≧5 sec. above the normal plasma control and a 1:1 mixture of patient's plasma with normal plasma did not correct the prolonged APTT in a dilute APTT assay. Two lupus anticoagulant-containing plasmas were also obtained from SLE patients receiving intravenous heparin therapy.

Factor deficient plasmas were obtained in lyophilized form from Organon and in fresh frozen form from the Coagulation Laboratory of Montreal General Hospital. Anti-factor antibody-containing plasmas from hemophiliac patients with anti-Factor VIII antibodies were supplied by Montreal Children's Hospital. Plasmas of patients receiving intravenous heparin therapy were provided by the Coagulation Laboratory of Montreal General Hospital. All plasmas were frozen at −70° C. until required for assay.

Phosdholidid Inhibition of the Diluted APTT Assay

Clotting times were determined using the General Diagnostics Coag-a-mate (R) ISO single channel instrument (Warner-Lambert Co., Morris Plains, N.J.), a semi-automated photo-optical clot detection system. Seventy-five ul of plasma was mixed with an equal volume of of the stock suspension of DOPE (4 mg/ml) −50 mol % desoxycholate in Hepes buffer and incubated for 10 min. in a 37° C. water bath. Fifty ul of this mixture was then diluted with an equal volume of freshly reconstituted Verify normal citrated plasma in a cuvette in a disposable circular test tray (obtained from Organon). One hundred ul of the 1/32 dilution of APTT reagent, which had been prewarmed to 37° C., was then added and the mixture incubated for 5 min. at 37° C.

After incubation of the sample, 100 ul of 25 mM $CaCl_2$ was added to the cuvette through the reagent incubation arm of the Coag-a-mate (R) machine, initiating the clotting sequence. The clotting time was displayed on the Coag-a-mate (R) digital timer and recorded. All samples were tested in duplicate and on two separate occasions to ensure reproducibility. The ability of the stock DOPE-desoxycholate suspension ("DOPE-desoxy") to inhibit anticoagulant activity when compared to stock desoxycholate/Hepes solution ("desoxy") was calculated using the following formula, designated Equation 1. (In those cases in which comparative stock desoxycholate/Hepes solutions were not tested, as indicated by "nt" in the test results, the plasma+buffer APTT value was used in place of the plasma+desoxy APTT value):

$$\% \text{ Inhibition} = \frac{\text{APTT (plasma + desoxy)} - \text{APTT (plasma + DOPE-desoxy)}}{\text{APTT (plasma + desoxy)} - \text{APTT (Verify + DOPE-desoxy)}} \times 100\%$$

EXAMPLE 1

EFFECT OF DOPE-DESOXYCHOLATE SUSPENSION ON LUPUS ANTICOAGULANT ACTIVITY IN SLE PLASMA

Five samples of plasma containing lupus anticoagulant (LA) and one Verify sample were tested by the APTT assay. Each sample was tested after incubation with 1) a Hepes buffer control ("Hepes"); 2) the stock desoxycholate/Hepes solution ("desoxy") (samples 1 to 3 only); and 3) the stock DOPE-desoxycholate suspension ("DOPE-desoxy"), respectively. For each sample, the clotting time after incubation in the DOPE-desoxy suspension was compared to the clotting time after incubation in desoxy/Hepes (samples 1–3) or plain Hepes buffer (samples 4–5), to determine the % inhibition of the APTT test, calculated in accordance with Equation 1 above. The results are presented in Table I.

TABLE I

| Plasma Sample | APTT (sec) | | | % Inhibition of APTT |
|---|---|---|---|---|
| | + Hepes | + Desoxy | + Dope-Desoxy | |
| Verify | 39.0 | 38.8 | 40.2 | |
| LA | | | | |
| 1 | 57.4 | 56.3 | 42.3 | 87.0 |
| 2 | 59.7 | 58.9 | 43.5 | 82.3 |
| 3 | 66.5 | 64.1 | 45.2 | 94.5 |
| 4 | 53.4 | nt | 44.4 | 89.1 |
| 5 | 64.6 | nt | 44.4 | 94.8 | nt - not tested

As would be expected, the lupus anticoagulant in Hepes buffer greatly prolonged the clotting time of the plasma sample in the APTT test. Incubation with the desoxycholate/Hepes solution had only a negligible effect on clotting times when compared to the Hepes buffer controls. On the other hand, incubation with the DOPE-desoxycholate suspension significantly inhibited 80 to 95 percent of the effect of the lupus anticoagulant, so that the coagulation times were only slightly longer than that of the Verify sample.

EXAMPLE 2

EFFECT OF DOPE-DESOXYCHOLATE SUSPENSION ON ANTI-FACTOR ANTIBODY PLASMAS

Five samples of plasma containing anti-Factor VIII and one Verify sample were tested by APTT assay following the same procedure used in Example 1. The results are presented in Table II:

TABLE II

| Plasma Sample | APTT (sec) | | | % Inhibition of APTT |
|---|---|---|---|---|
| | + Hepes | + Desoxy | + Dope-Desoxy | |
| Verify A-F VIII | 39.8 | 40.4 | 42.5 | |
| 1 | 51.5 | 50.1 | 47.9 | 22.6 |
| 2 | 65.4 | 61.3 | 67.1 | 0 |
| 3 | 66.8 | 64.9 | 59.8 | 24.5 |
| 4 | 49.0 | nt | 49.5 | 0 |
| 5 | 49.6 | nt | 50.2 | 0 | nt - not tested

As in Example 1, the results in Table II show that anti-Factor VIII samples had significantly prolonged APTT coagulation times, as compared to the Verify sample. However, in this case, incubation with the DOPE-desoxycholate suspension had little or no effect on the prolonging of coagulation time caused by anti-Factor VIII. This demonstrates the selectivity of the DOPE-desoxycholate for lupus anticoagulant as opposed to other anticoagulant factors. Again, incubation with desoxycholate/Hepes solution was found to have only a negligible ingibitory effect on the prolonged coagulation times.

EXAMPLE 3

EFFECT OF DOPE-DESOXYCHOLATE SUSPENSION ON FACTOR DEFICIENT PLASMAS

Six samples of plasmas deficient in particular clotting factors and one Verify sample were tested by the procedure of Example 1. Each sample was composed of 80% of the specified plasma and 20% of the Verify plasma. Tests were conducted on factor-deficient plasmas obtained from patients (labeled "F." factor numbers in the following table) and on commercial factor deficient plasmas obtained from Organon (labeled "C. F." factor numbers in the table). The results are presented in Table III:

TABLE III

| Plasma Sample | APTT (sec) | | | % Inhibition of APTT |
|---|---|---|---|---|
| | + Hepes | + Desoxy | + Dope-Desoxy | |
| Verify | 39.4 | 39.0 | 40.0 | |
| F. XII | 48.1 | 49.8 | 47.1 | 27.5 |
| C. F. VIII | 67.9 | 68.6 | 61.4 | 25.2 |
| F. XI | 79.3 | nt | 72.8 | 16.5 |
| C. F. XI | 70.8 | 64.9 | 65.5 | 0 |
| C. F. XII | 59.8 | 55.3 | 55.9 | 0 |
| C. F. IX | 69.2 | 69.8 | 68.4 | 4.7 | nt - not tested

As in the previous examples, the plasma deficient samples all showed prolonged APTT clotting times as compared to the Verify sample. For these factor deficient samples, incubation with the DOPE-desoxycholate suspension also showed negligible effect on the clotting time. In each case, incubation with the desoxycholate/Hepes solution showed only negligible effect on the APTT time. Again, this shows how DOPE in combination with desoxycholate can be used to distinguish clotting inhibition caused by lupus anticoagulant from that caused by a deficiency of a particular clotting factor, and that the desoxycholate does not interfere with this determination.

EXAMPLE 4

EFFECT OF DOPE-DESOXYCHOLATE SUSPENSION ON HEPARINIZED PLASMAS

In this example, four samples of heparinized plasmas, a fifth heparinized lupus anticoagulant-containing plasma, and a Verify sample were tested in accordance with the procedure of Example 1. The results are presented in Table IV:

TABLE IV

| Plasma Sample | APTT (sec) | | | % Inhibition of APTT |
|---|---|---|---|---|
| | + Hepes | + Desoxy | + Dope-Desoxy | |
| Verify | 37.5 | 37.6 | 40.8 | |
| Hep. 1 | 45.1 | 54.2 | 54.3 | 0 |
| Hep. 2 | 47.1 | 55.4 | 56.6 | 0 |
| Hep. 3 | 50.6 | 50.5 | 51.4 | 0 |
| Hep. 4 | 51.6 | 51.7 | 53.0 | 0 |
| LA + Hep. | 60.1 | 60.4 | 54.5 | 20.9 |

The test results show the normal anticoagulation effect of heparin on plasma samples. In this example, the pre-incubation of heparinized samples with desoxycholate/Hepes solution or with DOPE-desoxycholate suspension was found to have no inhibitory effect on the clotting prolongation caused by the heparin. In fact, the pre-incubations even caused a further prolonging of clotting times in some samples. In the last sample, clotting was prolonged by both heparin and lupus anticoagulant. In this case, the DOPE-desoxycholate pre-incubated sample showed some inhibition of the clotting time prolongation, while the desoxycholate pre-incubated sample showed no such inhibition. This demonstrates the selectivity of the DOPE-desoxycholate for lupus anticoagulant, as opposed to heparin anticoagulant, and also demonstrates that desoxycholate by itself does not affect the lupus anticoagulant clotting prolongation.

EXAMPLE 5

DRIED-DOWN DOPE-DESOXYCHOLATE

In this example, 38 ul of the 50 mg/ml desoxycholate stock solution were combined with 90 ul of the 50 mg/ml DOPE stock solution. Additional 1:1 $CHCl_3$:MeOH solvent was added to make up 1 ml of solution. Then 0.1 ml of this solution was pipetted into ten individual 12×75 mm test tubes, and the solvent was removed by evaporation under dry nitrogen for 30 minutes. This left a dried-down coating of DOPE in combination with the desoxycholate on the inside of the test tubes (hereinafter referred to as "DOPE-desoxycholate tubes"). (These Dope-desoxycholate tubes can be used immediately or frozen and stored for future use at, for example, −70° C.) For comparative tests with desoxycholate, 38 ul of the 50 mg/ml desoxycholate stock solution was mixed with sufficient 1:1 $CHCl_3$:MeOH solvent to make up 1 ml of solution. Then 0.1 ml aliquots of this solution were pipetted into ten test tubes and the tubes dried down as above (hereinafter referred to as "desoxycholate tubes"). In this manner, a supply of tubes containing dried-down DOPE-desoxycholate and dried-down desoxycholate were prepared for the following APTT assay tests.

In the following tests, 150 ul samples of each plasma were added to an empty tube (identified as "neat" in the test results), a desoxycholate tube, and a DOPE-desoxycholate tube, respectively. In these samples, it is the plasma itself which is the aqueous medium in which the DOPE-desoxycholate combination is suspended. These DOPE-desoxycholate samples contained 3 mg/ml DOPE and 43 mol % desoxycholate. All the samples were pre-incubated for 15 minutes in a 37° C. water bath.

APTT assays were then conducted on the samples by the process described above. Fifty ul of each sample was diluted with an equal volume of freshly reconstituted Verify normal citrated plasma in a cuvette in a disposable circular test tray (obtained from Organon). One hundred ul of the 1/32 dilution of APTT reagent, which had been prewarmed to 37° C., was then added and the mixture incubated for 5 min. at 37° C. The results of the tests are presented in Table V:

TABLE V

| Plasma Sample | APTT (sec) | | | % Inhibition of APTT |
|---|---|---|---|---|
| | + Hepes | + Desoxy | + Dope-Desoxy | |
| Verify | 39.3 | 36.2 | 40.4 | |
| LA | | | | |
| 1 | 61.5 | 57.5 | 43.3 | 83.0 |
| 2 | 57.5 | 57.5 | 40.7 | 98.2 |
| 3 | 52.7 | 49.8 | 39.6 | 100 |
| Anti-Factor VIII | | | | |
| 1 | 50.1 | 50.1 | 51.9 | 0 |
| 2 | 57.0 | 56.1 | 56.2 | 0 |
| 3 | 45.0 | 44.3 | 45.6 | 0 |
| 4 | 45.9 | 45.0 | 46.2 | 0 |
| Factor Deficient | | | | |
| C. F. XI | 67.8 | 66.0 | 64.7 | 5.0 |
| C. F. XII | 59.4 | 57.2 | 57.3 | 0 |
| Hep. | | | | |
| 1 | 62.0 | 60.5 | 62.6 | 0 |
| 2 | 51.4 | 50.5 | 51.4 | 0 |
| 3 | 57.0 | 56.5 | 62.4 | Prolonged |
| 4 | 50.2 | 53.6 | 71.0 | Prolonged |

As with Examples 1 to 4, the results in the above Table V show the selectivity of the DOPE-desoxycholate pre-incubation for inhibiting the prolongation of the clotting in the APTT assay caused by lupus anticoagulant as opposed to other anticoagulant factors.

EXAMPLE 6

USE OF COATED BEADS TO MIMIC HEXAGONAL ($H_{II}$) PHOSPHOLIPIDS

Figure 3A:
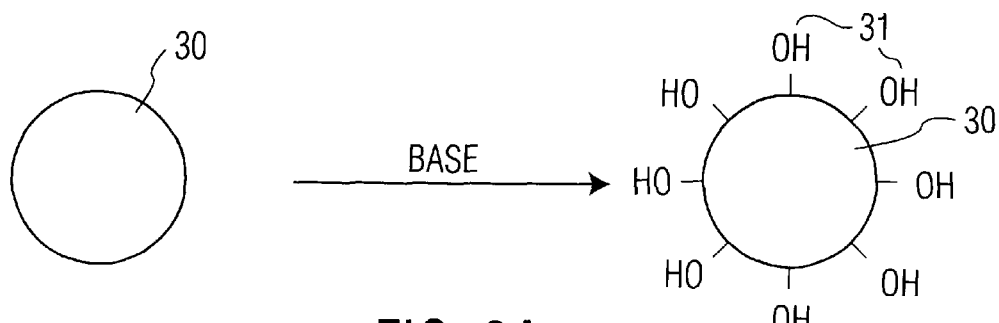
FIG. 3 is a schematic representation of a method of coating gold beads with a lipid monolayer in accordance with the present invention.
Figure 3B:
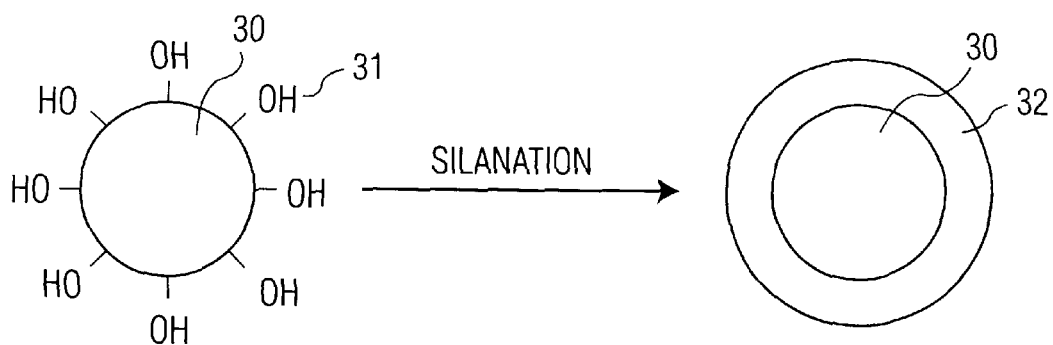
Figure 3C:
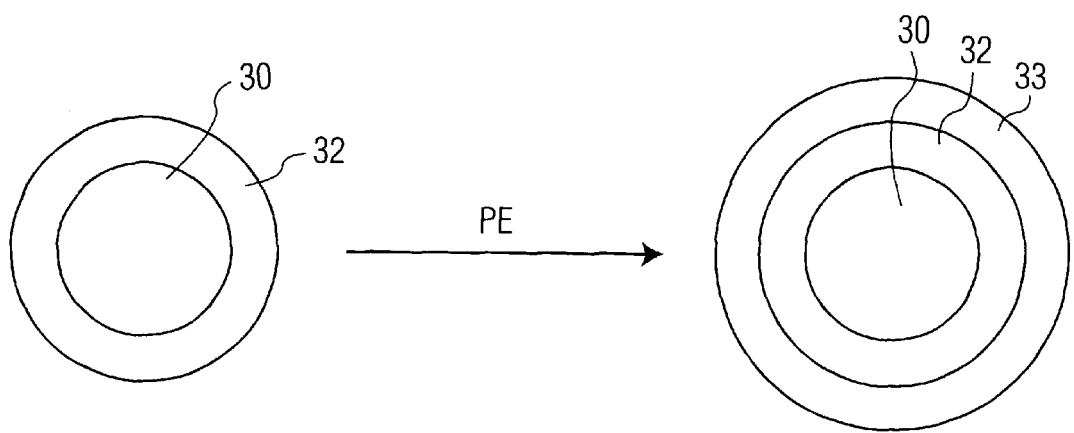

The present examples will be described with reference to the schematic process flow sheet for a single bead presented in FIG. 3. As shown in FIG. 3A, a gold bead 30, is first surface activated by exposure to 5 mM NaOH to form —OH active sites 31 on the surface of the gold. FIG. 3B shows that the activated bead is then coated with a silane bonding layer 32, and as shown in FIG. 3C, a monolayer 33 of POPE is then applied to the silane coated gold beads. The radius of gold beads coated in this manner was determined to be about 6.5 nm, approximating the radius of curvature of the hexagonal ($H_{II}$) tubular structures of EPE.

In the following examples, the gold beads used were 5.0-nm diameter beads obtained as a "colloidal gold" dispersion in 3 mM sodium azide water solution from Polysciences, Inc., Warrington, Pa. The POPE was obtained from Avanti Polar Lipids (Birmingham, Ala.), and the DMOAP was obtained from Hüls America/Petrarch Systems, as discussed above.

A more detailed description of the procedure used for preparing the 5.0-nm gold beads coated with POPE is as follows:

A 6.36-mg batch of 5.0-nm gold beads in 3 mM sodium azide were put into a 38-ml polyallomer ultracentrifuge tube. The beads were spun down at 27,000 rpm (132,000×g) for 30–60 minutes. The supernatant was decanted and saved, leaving the beads as a pellet in the tube. The pelleted beads were then rinsed with distilled water ($dH_2O$) by dispersing the beads in water and spinning them down at 43,000 rpm (150,000×g) for 30 minutes, repeating this step three times. The rinsed beads were then washed by dispersing in detergent (Liqui-nox), sonicating for about 15–20 minutes, and spinning down at 150,000×g for 30 minutes. The beads were then rinsed with $dH_2O$ and spun down three times as above.

To activate the surface of the beads, the beads were dispersed in a sufficient amount of 5 mM NaOH to cover them, and sonicated for 15–20 minutes, followed by spinning down at 150,000×g for 30 minutes. The beads were then rinsed with $dH_2O$ and spun down three times as above. The surface of the beads was silanized by incubating them in a 50% (v/v) solution of DMOAP in water for 30 minutes, with occasional sonication. The beads were then rinsed with $dH_2O$ and spun down three times as above. The silanized beads were then coated with the phospholipid by adding 6 mg of POPE dissolved in hexane to the beads and sonicating to disperse the beads in the hexane. The hexane was removed by evaporation with a stream of nitrogen gas, followed by evacuation at 150 mtorr for 1–4 hours to remove as much solvent as possible.

The coated beads were then hydrated in enough 20 mM tris-maleate at pH 7.2 to cover them, with brief sonication to remove the mixture from the walls of the tube. This mixture was then layered onto a discontinuous 15–30% sucrose density gradient and spun for 1–2 hours at 150,000×g. The coated beads pelleted at the bottom of the tube, while the excess free lipid floated at the 15%–30% interface. The supernatant was decanted, saving the free lipid as a control sample. The coated beads were then rinsed in tris-maleate, as above, and spun down at 150,000×g for 30 minutes.

The amount of lipid deposited on the surface of the gold beads was determined using a fluorescence assay technique. In this assay, the beads were coated with POPE spiked with 0.1 weight percent NBD-PE (N-(7-nitrobenz-2-oxa-1,3-diazol-4-yl)-dipalmitoyl-L-alpha-PE). After separating the unadhered lipid from the gold beads by sucrose density gradient centrifugation, the beads were examined by fluorescence spectroscopy between 500–830 nm. The excitation wavelength was 465 nm. The amount of lipid adhered to the beads was determined by comparing the bead spectrum to that of a control POPE/NBD-PE mixture consisting of 1.0 mg POPE/1.0 ug NBD-PE. All areas were determined by cutting and weighing. Based on this assay technique, it was determined that the gold beads had an average of 1.113 monolayers of POPE on the surface of the beads, closely approximating the proposed monolayer structure.

APTT Test Trials Using POPE Coated Beads:

The POPE coated gold beads, prepared as above, were tested for their effectiveness for use in lupus anticoagulant determinations. APTT tests were conducted in accordance with the procedure of Example 1. Tests were conducted on a control of verify normal plasma, two samples of lupus anticoagulant-containing plasma obtained from different patients, and antifactor antibody-containing plasma. For each plasma APTT determinations were conducted without beads, with uncoated beads, with POPE liposomes (not in hexagonal ($H_{II}$) form), and the POPE coated beads. The results are set forth in Table VI:

TABLE VI

| Plasma Sample | APTT (sec) | | | |
|---|---|---|---|---|
| | Without Beads | Uncoated Beads | POPE Liposomes | Coated Beads |
| Verify | 40.5 | 38.8 | 40.2 | 40.7 |
| Lupus Anti. 1 | 53.6 | 52.9 | 51.3 | 41.6 |
| Lupus Anti. 2 | 85.7 | 78.3 | 74.7 | 51.8 |
| Antifactor Anti. | 65.3 | 63.7 | 61.2 | 63.9 |

These results show the effectiveness of the POPE coated beads in counteracting the inhibition effects of lupus anticoagulant on the APTT test results, without affecting the inhibition effects of the antifactor antibody. This is the same selectivity which characterizes the use of hexagonal ($H_{II}$) phospholipids in lipid-dependent diagnostic assays, as described in U.S. Pat. No. 4,666,831. Thus, it has been shown that the beads coated with a monolayer of phosphatidylethanolamine can be used in place of hexagonal ($H_{II}$) phospholipids in such diagnostic assays.

The terms and expressions which have been employed are used as terms of description and not of limitation, and there is no intention in the use of such terms and expression of excluding any equivalents of the features described or portions thereof, but it is recognized that various modifications are possible within the scope of the invention claimed.

What is claimed is:

1. A method for determining the presence of lupus anticoagulants in a patient's plasma which comprises the steps of:
    (a) obtaining first and second samples of the patient's plasma;
    (b) combining a detergent and a phospholipid so as to obtain an aqueous suspension comprising particles containing the detergent and the phospholipid:
    (c) incubating the first sample with the aqueous suspension;
    (d) performing a lipid-dependent diagnostic assay on both the first and second samples, the assay producing a positive reading when used on to assay a sample which contains lupus anticoagulants; and
    (e) comparing the results of the assays performed on the first and second samples, the presence of a normal result for the first sample and a positive result for the second sample being indicative of the patient having lupus anticoagulants;
    wherein the phospholipid has a hexagonal ($H_{II}$) phase organization in aqueous detergent-free media, wherein the detergent is a lupus assay-compatible detergent, wherein the particles comprising the phospholipid and detergent have diameters of less than about 50 nm, wherein the phospholipid remains in suspension at a temperature of 25° C. for at least one hour, and wherein the detergent, in combination with the phospholipid, is capable of inhibiting lupus anticoagulant, and not interfering with the anticoagulant effect of heparin, anti-Factor antibodies and factor deficiencies.

2. The assay of claim 1 wherein the test sample is human plasma and the assay is a coagulation test.

3. The assay of claim 2 wherein the assay is an assay measuring activated partial thromboplastin time.

4. The assay of claim 2 wherein the phospholipid is a phosphatidylethanolamine selected from the group consisting of dioleoyl phosphatidylethanolamine, egg phosphatidylethanolamine, and bovine phosphatidylethanolamine.

5. The assay of claim 1 wherein the detergent is a salt and wherein the concentration of the detergent in the mixture comprising the detergent and the phospholipid is about 40 to 50 mole percent.

6. The assay of claim 5 wherein the salt is sodium desoxycholate.

7. The assay of claim 1 wherein the phospholipid is dioleoylphosphatidylethanolamine.

8. A method of reducing false positive results from a lipid-dependent diagnostic assay performed on a blood sample obtained from a patient having an autoimmune disorder characterized by the presence of anti-phospholipid antibodies, which comprises pre-incubating the sample prior to conducting the assay with an aqueous phase comprising a suspended phospholipid, wherein the phospholipid has a hexagonal ($H_{II}$) organization in aqueous detergent free media, wherein the aqueous phase comprises a detergent, wherein the phospholipid remains suspended in the aqueous phase for at least one hour at a temperature of about 25 deg. C. and wherein the phospholipid and detergent are not capable of interfering with the anticoagulant effect of heparin, anti-Factor antibodies and factor deficiencies.

9. The method of claim 8, wherein the assay is an activated partial thromboplastin time, prothrombin time, Russell viper venom time or a cardiolipin-dependent syphilis assay.

10. The method of claim 9, wherein the assay is a coagulation test performed on human plasma.

11. The method of claim 8, wherein the autoimmune disorder is systemic lupus erythematosus, Hashimoto's thyroiditis or rheumatoid arthritis.

12. The method of claim 11, wherein the autoimmune disorder is systemic lupus erythematosus.

13. The method of claim 8, wherein the phospholipid is a phosphatidylethanolamine.

14. The method of claim 13, wherein the phosphatidylethanolamine is dioleoyl phosphatidylethanolamine, egg phosphatidylethanolamine or bovine phosphatidylethanolamine.

15. The method of claim 14, wherein the phosphatidylethanolamine is egg phosphatidylethanolamine.

16. The method of claim 8, wherein the detergent comprises a desoxycholic acid salt.

17. The method of claim 14, wherein the detergent comprises sodium desoxycholate.

18. The method of claim 8, wherein the assay is a coagulation test performed on human plasma obtained from a patient afflicted with systemic lupus erythematosus, the phospholipid is a phosphatidylethanolamine and the detergent is sodium desoxycholate.

19. A method of determining the presence of lupus anticoagulants in a patient's plasma which comprises the steps of:
    (a) obtaining a first and a second sample of a patient's plasma:
    (b) incubating the first sample with an aqueous suspension comprising a phosphatidylethanolamine;
    (c) performing a lipid-dependent diagnostic assay on both the first and the second sample the assay producing a positive reading when used on a sample which contains lupus anticoagulants; and
    (d) comparing the results of the assays performed on the first and second samples, the presence of a normal result for the first sample and a positive result for the second sample being indicative of the presence of lupus anticoagulants in the plasma:

wherein;
the suspension of the phosphatidylethanolamine further comprises a lupus assay-compatible detergent;
the phosphatidylethanolamine remains in suspension at a temperature of 25° C. for at least one hour;
the detergent, in combination with the phosphatidylethanolamine, is capable of inhibiting lupus anticoagulant, and not interfering with the anticoagulant effect of heparin, anti-Factor antibodies and factor deficiencies; and,
the phosphatidylethanolamine is coated on a substrate bead, wherein the bead is composed of an inert material and wherein the bead has a diameter of from about 1 nm 50 nm.

20. The method of claim 19, wherein the bead has a diameter of from about 5 nm to 20 nm.

21. The method of claim 19, wherein the bead is a gold bead and wherein the bead comprises a bonding layer between the bead surface and the phospholipid.

22. The method of claim 21, wherein the bonding layer comprises a silane having a polar headgroup and one or two nonpolar tails.

23. The method of claim 22, wherein the silane comprises N,N-dimethyl-N-octadecyl-3-aminopropyltrimethysilyl chloride.

24. The method of claim 19, wherein the phosphatidylethanolamine is in a hexagonal phase.

25. The method of claim 19, wherein the phosphatidylethanolamine is a bilayer-forming phosphatidylethanolamine.

26. The method of claim 19, wherein the phosphatidylethanolamine is egg phosphatidylethanolamine, dioleoyl phosphatidylethanolamine, bovine phosphatidylethanolamine or palmitoyloleoyl phosphatidylethanolamine.

27. The method of claim 26, wherein the phosphatidylethanolamine is palmitoyloleoyl phosphatidylethanolamine.

28. The method of claim 19, wherein the phospholipids are coated on a gold bead having a diameter of about 13 nm, wherein the bead has a bonding layer between the surface and the phospholipids and wherein the bonding layer comprises a silane comprising N,N-dimethyl-N-octadecyl-3-aminopropyltrimethysilyl chloride.

* * * * *